(12) United States Patent
Orwar et al.

(10) Patent No.: US 7,393,680 B2
(45) Date of Patent: Jul. 1, 2008

(54) COMBINED ELECTROPORATION AND MICROINJECTION METHOD FOR THE PENETRATION OF LIPID BILAYER MEMBRANES

(75) Inventors: Owe Orwar, Hovås (SE); Mattias Karlsson, Göteborg (SE); Daniel Chiu, Seattle, WA (US)

(73) Assignee: Cellectricon AB, Gothenburg (SE)

( * ) Notice: Subject to any disclaimer, the term of this patent is extended or adjusted under 35 U.S.C. 154(b) by 212 days.

(21) Appl. No.: 10/399,584

(22) PCT Filed: Oct. 19, 2001

(86) PCT No.: PCT/SE01/02301

§ 371 (c)(1),
(2), (4) Date: Jul. 23, 2003

(87) PCT Pub. No.: WO02/33066

PCT Pub. Date: Apr. 25, 2002

(65) Prior Publication Data

US 2004/0029101 A1    Feb. 12, 2004

(30) Foreign Application Priority Data

Oct. 20, 2000  (SE) .................... 0003841

(51) Int. Cl.
C12M 1/42 (2006.01)
(52) U.S. Cl. .................................... 435/285.2
(58) Field of Classification Search ............ None
See application file for complete search history.

(56) References Cited

U.S. PATENT DOCUMENTS

| | | | | |
|---|---|---|---|---|
| 4,784,737 | A * | 11/1988 | Ray et al. | 435/455 |
| 5,859,327 | A * | 1/1999 | Dev et al. | 800/292 |
| 5,874,268 | A | 2/1999 | Meyer | 435/173.6 |
| 6,079,230 | A * | 6/2000 | Kong | 65/160 |
| 6,261,815 | B1 | 7/2001 | Meyer | 435/173.6 |
| 2002/0061589 | A1 | 5/2002 | King et al. | 435/446 |
| 2002/0062126 | A1 | 5/2002 | Lewis et al. | 606/45 |
| 2002/0127723 | A1 | 9/2002 | Palermo | 435/461 |
| 2002/0133137 | A1 | 9/2002 | Hofmann | 604/501 |
| 2002/0160437 | A1 | 10/2002 | Meyer | 435/15 |
| 2002/0198485 | A1 | 12/2002 | Dev et al. | 604/20 |
| 2002/0198512 | A1 | 12/2002 | Seward | 604/522 |
| 2003/0009113 | A1 | 1/2003 | Olson | 600/573 |
| 2003/0009148 | A1 | 1/2003 | Hayakawa | 604/501 |
| 2003/0017598 | A1 | 1/2003 | Burke et al. | 435/461 |

FOREIGN PATENT DOCUMENTS

| | | |
|---|---|---|
| JP | 19950133907 | 5/1995 |
| WO | WO 99/24110 | 5/1999 |
| WO | WO 00/34434 | 6/2000 |
| WO | WO 01/07583 | 1/2001 |
| WO | WO 01/48180 | 5/2001 |
| WO | WO 02/31171 | 4/2002 |
| WO | WO 02/100459 | 12/2002 |

OTHER PUBLICATIONS

Karlsson, et al., "Electroinjection of Colloid Particles and Biopolymers into Single Unilamellar Liposomes and Cells for Bioanalytical Applications", Anal. Chem., 72, 5857-5862 (2000).
Swartz, et al., "Sparking New Frontiers: Using in Vivo Electroporation for Genetic Manipulations" Development Biology 233, 13-21 (2001).
Lundqvist, et al., "Altering the biochemical state of individual cultured cells and organelles with ultramicroelectrodes", Proc. Natl. Acad. Sci. USA, vol. 95, pp. 10356-10360, Sep. 1998.
Needham, et al., "Electro-mechanical permeabilization of lipid vesicles, Role of membrane tension and compressibility", Biophys J. ® Biophysical Society, vol. 55, May 1989, 1001-1009.
Wick, et al., "Microinjection into giant vesicles and light microscopy investigation of enzyme-medicated vesicle transformations", Chemistry & Biology, Feb. 1996, 3:105-11.
Clark, et al., "Optical Nanosensors for Chemical Analysis inside Single Living Cells. 1. Fabrication, Characterization, and Methods for Intracellular Delivery of Pebble Sensors", Anal. Chem., 1999, 71, 4831-4836.

\* cited by examiner

*Primary Examiner*—Cecilia Tsang
*Assistant Examiner*—Christina Marchetti Bradley
(74) *Attorney, Agent, or Firm*—David G. Conlin; Jeffrey L. Kopacz; Edwards Angell Palmer & Dodge LLP

(57) ABSTRACT

Disclosed is a method for penetration of lipid bilayer membranes in order to insert at the tip of a hollow needle-shaped object, such as a micropipet-, into a container formed of a lipid bilayer membrane, wherein said container is placed between said needle-shaped object, with the tip of said needle-shaped object placed in contact with said conainer in such a way that it applies a mechanical force to the lipid membrane of said container, thus mechanically straining it, and a second electrode, whereupon a transient electric pulse of $1$-to-$10^3$ V/cm is applied between the electrodes, resulting in a focused electrical field over said container C which induces a dielectric breakdown of the lipid bilayer causing the needle-shaped object to penetrate the container. Disclosed is also an electroinjection method based on the above method, wherein substances are introduced through the needle-shaped object and into the container after penetration of the needle-shaped object.

37 Claims, 5 Drawing Sheets

COMBINED ELECTROPORATION AND MICROINJECTION METHOD FOR THE PENETRATION OF LIPID BILAYER MEMBRANES

This Application claims benefit of international application PCT/SE01/02301, filed Oct. 19, 2001 and to Swedish Application No. 0003841-4, filed Oct. 20, 2000.

FIELD OF THE INVENTION

The present invention relates to a method for the penetration of lipid bilayer membranes in order to insert tips of needle-shaped objects into lipid membrane enclosed containers, such as cells and liposomes. The invention also relates to a method for the injection of a substance into a lipid bilayer container, such as a cell, or more precisely to a microinjection method utilizing the concept of electromechanical destabilization for the efficient loading of substances, such as biopolymers, colloidal particles, and other biologically relevant molecules, into single cell-sized lipid bilayer containers.

BACKGROUND OF THE INVENTION

Today, there is a growing interest in inserting microelectrodes, microcapillaries and micropipet-tip-sensors into single cells. There is also a growing interest in incorporating sub-micron-sized sensing, sampling, and signal-amplifying particles, as well as large biopolymers into single cells and liposomes. Several ultrasensitive detection and sensing methods are based directly or indirectly on the use of colloidal particles. Examples include quantum dot bioconjugate sensors[1,2], the family of Probes Encapsulated By Biologically Localized Embedding (PEBBLE) sensors,[3] and silver (Ag) and gold (Au) colloids for use in Surface Enhanced Raman Spectroscopy (SERS) measurements[4-6]. One of the main limitations for practically using these techniques is the difficulty of noninvasive and quantitative introduction of colloidal particles into the cellular interior[7]. Furthermore, it would be attractive to direct the introduction of particles into specific subcellular compartments such as the cytosol, nucleus, or even organelles of individual cells.

GUVs are cell-sized liposomes composed of a single lipid bilayer with an entrapped aqueous compartment[8]. Such liposomes are attractive to use as ultra-small reaction containers in which the reaction under study is confined and separated from the external medium. As such they can be used for studies of biochemical reaction dynamics in compartments mimicking a natural intracellular-intraorganellar environment[9-12].

For use as reaction containers, it is necessary to load vesicles with reactants, including biopolymers like DNA and colloid particles or organelles (synthetic or naturally derived). Loading of liposomes can, in principle, be performed by adding the particles during the preparation of the vesicles, since they upon formation trap a part of the medium in which they are formed. The trapping efficiency for small liposomes is, however, limited even for low-molecular-weight compounds and, entrapment of larger structures such as colloids, is of very low probability[13,14].

Another approach for liposome-loading is to introduce the materials into preformed vesicles by using micromanipulation-based techniques developed for loading of single cells. One such technique that is feasible to use is the microinjection technique[15].

By using microneedles made out of pulled glass capillaries with outer tip-diameters in the range of 200-500 nm, it is possible to penetrate the membrane wall of a liposome, or cell, and eject controlled volumes of a desired reagent inside the vesicle[16]. Injection volumes are typically in the picoliter to attoliter range and controlled by regulation of injection-time and injection-pressure. The pressure is usually generated by utilization of pressurized-air or oil-hydraulic systems.

All microinjection techniques are based on mechanical permeabilization of lipid membranes. When a mechanical point-load is applied, e.g. by a capillary, onto the membrane of a liposome or cell, the membrane is forced to stretch and the isotropic membrane tension, working in the plane of the membrane, is increased. At sufficiently high membrane tension, the structural integrity of the liposome, or cell, is momentarily lost as holes are formed in the membrane, releasing internal fluid in order to counteract the increase in membrane tension. This membrane rupture occurs at the site of the highest mechanical load, which is the loci where the point-load is applied, thus allowing the insertion of a microinjection capillary into the interior of the liposome or cell.

Whereas microinjection works well with certain cell-types and multilamellar liposomes, there are a few drawbacks to the microinjection techniques with unilamellar vesicles and many cell types. Lipid membrane bilayers are, typically, very elastic and the absence of internal supporting structures in unilamellar liposomes make them very difficult to penetrate by mechanical means. The outer diameter of a tip suitable for injection into thin-walled liposomes and smaller cells is about 200 nm, and the inner diameter is typically in the range of only 100 nm[16,17]. Such tips are very fragile and extremely difficult to view in a light microscope, making positioning difficult. The main drawback of using small inner-diameter injection tips is, however, the requirement of using ultrapure injection liquids in order to prevent clogging, limiting injection species to solutions of low- and medium-molecular-weight compounds. Micro-injection techniques are considered to be relatively invasive due to the large mechanical forces applied, inducing permanent membrane damage and even lysis of cells and liposomes.

An alternative approach to single-liposome or single-cell loading is to use microelectroporation[18]. This technique is based on the theory of electro-permeabilization. When exposing a liposome, or cell, to an electrical field, a potential drop is generated across the membrane. At sufficiently high field strength, the critical transmembrane potential $V_c$, of the membrane is exceeded, and small pores will form in the liposomal/cellular membrane due to dielectric membrane breakdown. The transmembrane potential $V_m$, at different loci on the membrane of a spherical vesicle during exposure to a homogeneous electric field of duration t, can be calculated from $$V_m = 1.5\, r_s E \cos\alpha (1-\exp(-t/\tau))$$

where E is the electric field strength, $r_s$ is the radius of the sphere, $\alpha$ is the angle in relation to the direction of the electric field, and $\tau$ is the capacitive-resistive time constant. Pore formation will occur at spherical coordinates exposed to the largest potential shift, which is at the poles facing the electrodes. Typical value for $V_c$ for a cell-sized vesicle is ~1V, and the corresponding electric field strength needed for exceeding the critical transmembrane potential $V_c$, is in the range of 1-10 kV/cm.

In microelectroporation, the analyte to be encapsulated is added to the exterior solution of the liposomes, or cells, and an electrical field is then applied locally, using microelectrodes. The amount of analyte that enters the vesicle is dependent on the analyte concentration gradient, membrane potential, duration of the applied field, and diffusion rate of the analyte[19]. Drawbacks to the electroporation technique are difficulties of quantitative loading, and loading of structures of sizes larger than the effective pore-diameter, which for electropermeabilized erythrocytes is in the range of 1-to-240 nm[20,21]. To improve quantitive loading, controlled amounts of analytes can be introduced via a small micropipette tip inserted into a hole pre-formed by electroporation (as described, for example, in JP 8322548). This approach, however, presents a number of disadvantages, including the need to apply a fairly strong electric field (~1V) to form a hole for tip insertion.

By combining electroporation and the application of a mechanical force onto a membrane vesicle, the strength of the applied electrical field needed for membrane permeabilization may be substantially reduced[25]. This phenomenon is sometimes referred to as electromechanical destabilization. It has been shown that electrical fields established over lipid bilayer membranes imposes an electrocompressive mechanical stress $\sigma_e$, acting on the lipid membrane. This force works normal to the plane of the membrane and leads to a decrease in membrane thickness. If assuming that a lipid membrane behaves as a capacitor, then the electro-compressive force is proportional to the voltage drop V, over the membrane and thus to the strength of the applied electric field $$\sigma_e = \frac{1}{2}\varepsilon\varepsilon_o \cdot \left(\frac{V}{h_e}\right)$$

where $\varepsilon$ is the relative dielectric constant and $\varepsilon_0$, is the permitivity and $h_e$, is the dielectric thickness of the membrane. The differential overall mechanical work dW, done on the lipid membrane is then simply the sum of the electro-compressive stress $\sigma_e$, and the isotropic membrane tension T, controlled by the amount of mechanical strain applied to the membrane $$dW = \left[T + \frac{1}{2}\varepsilon\varepsilon_o\left(\frac{V}{h_e}\right)\cdot h\right]dA$$

where h is the overall thickness of the lipid bilayer membrane, and dA is the change in membrane area. Consequently, when a mechanical strain is applied to a membrane vesicle, the trans-membrane potential needed to achieve permeabilization can be significantly reduced. Therefore this approach for membrane permeabilization may be even less invasive than electroporation since lower electric fields can be used, minimizing the risk of unwanted electrochemical reactions at the membrane surface of a cell or a liposome.

SUMMARY OF THE INVENTION

The present invention relates to a novel approach for inserting micropipet tips or any other cylindrical or hollow needle-shaped objects such as microelectrodes into containers formed of lipid bilayer membranes, such as cells and liposomes. The basic idea is to destabilize a mechanically strained lipid membrane container with electric pulses, facilitating the penetration of a micropipet.

The invention also relates to a method for introducing substances, such as large-molecular-weight compounds as well as colloid particles into containers formed of lipid bilayer membranes, such as GUVs, cells, and other similar membrane enclosed structures, by applying the concept of electromechanical membrane destabilization to a micropipet-assisted microinjection technique.

The unique advantage of such an arrangement arises from the combination of the high degree of spatial- and volume-control of microinjection and the efficient and non-invasive membrane permeabilization of electromechanical destabilization, thereby permitting quantitative introduction of analytes, and biologically relevant molecules and particles including colloids, into unilamellar liposomes and cells.

More specifically, the invention relates to a method for the penetration of a container formed or surrounded by at least one lipid bilayer membrane in order to insert the tip(s) of at least one hollow needle-shaped object into said container, wherein said container is placed between said at least one needle-shaped object, such as an electrolyte-filled micropipet, equipped with a first electrode, which preferably is an internal electrode, and a second electrode, wherein the tip of said at least one needle-shaped object is placed in contact with said container in such a way that said tip of said at least one needle-shaped object applies a mechanical force to the lipid bilayer membrane of said container, thus mechanically straining said container, whereupon a transient electric pulse of 1-to-10³ V/cm is applied between said first electrode and said second electrode, resulting in a focused electric field over said container, said electrical field inducing dielectric breakdown of the lipid bilayer causing the tip of said at least one needle-shaped object to penetrate the membrane of said container. Said at least one needle-shaped object is hollow and preferably constructed from an insulating material and is filled with an electrically conducting solution or with dispersion of a substance.

Preferably said first electrode is an internal electrode, i.e. located inside said hollow needle-shaped object. More preferably, the electrode is connected to said at least one needle-shaped object, which in this case is filled with an electrolyte, in which the electrode is placed. This embodiment has several advantages. For example, no electrochemical reaction is present at the tip of said at least one needle-shaped object since the electrode is located at a distance from the tip of said at least one needle-shaped object. The presence of such an electrochemical reaction would otherwise negatively affect the container, especially for cases when the container is a cell since the health and survivability of the cell then would deteriorate.

When the tip of the needle-shape object, such as a micropipet tip, has penetrated the container any of the solution or dispersion contained in the micropipet may be injected into the container by a variety of methods including pressure-induced and electro-osmotic flow, whereupon the micropipet may be removed, and this is used as a basis for the microinjection or electroinjection method according to the invention.

The electroinjection technique described here has several distinct advantages when compared to traditional stab-microinjection protocols. First of all, the technique is less invasive. Since the membrane is electrically destabilized, less mechanical force is needed for penetrating the lipid membrane with a micropipet or any other needle-shaped object of micro-dimensions. Consequently, there is less movement of the injection capillary when located inside a liposome or cell. Such movements may induce severe cell trauma caused by damages to the cellular matrix.

If compared to electroporation protocols, much lower transmembrane potentials are needed to achieve membrane destabilization, often the generated transmembrane potential is only a few mV (which is further explained in the examples below) two to three orders of magnitude smaller than the $V_m$ used in electroporation. Much lower electric fields translates into less electrically induced trauma to the cell, as well as minimizing the risk of unwanted electrochemical reactions at the membrane surface of a cell or a liposome. The usage of very low electric field strengths is, beside the fact that the membrane is under mechanical strain, also an effect of the highly focused electric field that is used. When a voltage is applied between the first and the second electrode, the non-conducting material of the needle-shaped object, such as a micropipet, directs the entire established electrical field through the tip-end opening of the pipet. Consequently, the part of the lipid membrane that is in contact with the tip-end of the needle-shaped object is exposed to the entire electrical field. The coordinates of maximum electro-compressive force thus spatially coincides with the loci where maximum mechanical force is applied.

The presented method for inserting the tips of needle-shape object, such as micropipets, into containers such as liposomes and cells is much more efficient than standard stab-microinjection protocols. As a consequence, large diameter micropipets can be used, allowing injections of large structures into unilamellar vesicles, as well as cells. From this, several possibilities arise. One attractive application is the quantitative introduction of nanosensors[1-3] or colloids, for SERS measurements[4-6] into cells for detection of molecules or for probing of intracellular structures. Another application is introduction of these particles into liposomal reaction containers. Such a procedure would allow studies of complex biochemical reactions where the formation of several products and intermediates simultaneously could be monitored. By incorporation of organelles (naturally or synthetically derived), or even bacteria into unilamellar vesicles it is possible to create highly advanced cell models. This is very attractive for studies of, for example, complex biochemical signaling systems that translocate between different intracellular compartments.

The electroinjection technique described here can be performed with very high success rates and allows sequential injection of multiple reagents into single liposomes and cells without noticeable leakage. Initiation of complex biochemical reactions inside the confines of a liposome or cell is therefore feasible. This also makes it possible to perform ultra-small-scale derivatization chemistry inside a liposome, or cell, for analyte labeling prior to microchemical separations.

If combined with the ultra-thin injection needles used for conventional microinjections[17], the method according to the present invention is a powerful technique for introduction of low- and medium-molecular-weight compounds into smaller cells or even organelles. This is due to the efficient membrane penetrative capacity of the electroinjection technique.

Another application is in the field of so called chip-array injections. Since the technique here presented is highly efficient in terms of membrane penetration capacity, it is feasible to construct an array injector system where a plurality of injection needles-tips are clustered together, arrayed, allowing parallel injection of a large number of cells simultaneously.

DETAILED DESCRIPTION OF THE INVENTION

As stated above, the present invention relates to a method for the penetration of lipid bilayer membranes in order to insert at least one tip of at least one needle-shaped object, such as a micropipet tip, into lipid membrane containers. More specifically the method is used for the penetration of a container constituted of at least one lipid bilayer, wherein said container first is placed between a hollow electrolyte filled, non-conducting needle-shape object, such as a micropipet, equipped with a first electrode, preferably an internal electrode, i.e. an electrode located inside said needle-shaped object, with the tip of said at least one needle-shaped object placed in contact with said container in such a way that said needle-shaped object applies a mechanical force to the lipid membrane of said container, thus mechanically straining said container, and a second electrode, whereupon, by the use of a low-voltage supply, a transient electric pulse of 1-to-$10^3$ V/cm is applied between said first electrode and said second electrode, thus establishing an electric field between said first and said second electrode, passing through the tip-end of the said needle-shaped object, resulting in a highly focused electrical field over the membrane part of said container that is in contact with said needle-shaped object, said electrical field inducing a local dielectric breakdown of the part of the mechanically strained lipid bilayer that is in contact with said needle-shaped object, causing the tip of the needle-shaped object to penetrate the membrane of the container.

Below, the term micropipet is used instead of needle-shaped object, however what is stated for the micropipet is valid also for other needle-shaped objects, such as other cylindrical or hollow needle-shaped objects of appropriate size, such as capillaries, ultra-thin injection needles, and microelectrodes. Below, the term also encompasses arrays of such needle-shaped objects, which, for example, may be mounted on a chip. Furthermore, the micropipet shall be filled with a conductive medium to allow electrical contact between the first electrode and the second electrode.

Said hollow, non-conducting micropipet, is filled with an electrically conducting solution or dispersion of a substance. When the micropipet has penetrated the container, any of the solution or dispersion of a substance contained in the micropipet may be injected into the container, after which the micropipet may be removed. In addition, the micropipet and microelectrode makes a pair of tweezers allowing for the manipulation and subsequent injection into the free-floating cells and liposomes.

Said substance contained in the micropipet and to be injected into a cell or liposome may be, for example, a low or medium molecular weight substance, such as a dye, a biopolymer, such a DNA, RNA or a protein, a colloidal particle, such as a colloidal bead, a nanosensor, an organelle, or a bacterium. The expression "low or medium molecular weight substance" relates to a substance with a molecular weight of up to a few kDa, such as up to 3 kDa. The substance is preferably injected into the container in the form of a solution or dispersion. A small volume, typically 50-to-500×$10^{-15}$ l, of the solution or dispersion is injected into the cell or other unilamellar container.

Said container shall be constituted of or surrounded by at least one lipid bilayer membrane. It may, for example, be a liposome, a vesicle, an organelle, a cell, a multilamellar liposome (MLV) or a giant unilamellar vesicle (GUV). The method according to the invention is particularly interesting for giant unilamellar vesicles and cells. The size of said unilamellar containers shall be organelle or cell-sized, i.e. 0.1-to-$10^3$ μm in diameter.

Said micropipet should be prepared from a nonconductive material in order to cintain and focus the applied electric field through the tip-end opening (the end closest to the container) of said micropipet, and may, for example, be a glass-, a quartz-, or a plastic-micropipet. The micropipet shall preferably have an outer diameter at the tip of 10 nm-to 100 μm, and an inner diameter, i.e. the diameter of the hollow space inside the micropipet, of 0.05 to 95 μm. Furthermore, the micropipet shall be filled with a conductive medium to allow electrical contact between the first electrode and the second electrode. The micropipet shall be equipped with a first electrode, preferably and internal, highly conductive electrode, such as Pt-, Ag-, Au-, or carbon fiber-electrode, however an electrode of any suitable conductive material may be used. The tip of the first electrode, located inside said micropipet, should be placed at a distance, preferably 0.5-to-1 cm, from the tip of the micropipet in irder to prevent direct contact between said first electrode and the lipid bilayer membrane of the container, thus protecting the membrane from electrochemically generated reactive species and/or gas bubbles that may form on the first electrode surface.

Said second electrode may be constituted of any suitable conductive material. It may, for example, be a carbon fiber-, a metal-, or a glass-micro-electrode. The second electrode shall preferably have a diameter in the end placed next to the container of approximately 1-to-$10^3$ μm. The first and second electrodes may be similar or different. It is also feasible to exchange the second electrode for a ground bath-type electrode.

The voltage pulse used to obtain the highly focused electric field between the first and second electrode, inducing the dielectric breakdown of the lipid bilayer shall be a transient electric pulse of a field strength 1-to-$10^3$ V/cm. Preferably a transient 0.01-to 10 ms, rectangular waveform dc-voltage pulse of 10-to 60 V/cm is used but other pulseforms as well as ac-voltage can be used.

Once the micropipet tip is inserted into the lipid membrane container, the micropipet can be used for several different purposes. For example, the micropipet can be used for sampling of intracontainer substances, the micropipet may also be a sensor such as a fiber optic- or electrochemical-microsensor used for intracontainer measurements or a microelectrode. Finally the micropipet can be used for injection of a substance into the container. When a substance is to be introduced into the container this can be done in many different ways. It is, for example, possible to use a technique based on electrophoresis, electroendoosmosis, gravity flow, or microinjection with the aid of compressed air or oil, or a thermo-sensitive expansion medium.

Once a substance is introduced into the lipid bilayer container, the container can be used for many different purposes. For example, when the substance introduced is colloidal particles, such as Ag or Au colloids, quantum dot bioconjugate sensors[1,2], or PEBBLE sensors[3] the container may be used in conjugation with an ultrasensitive detection or sensing method, such as SERS or quantitative fluorescence measurements, for detection of specific substances.

Another interesting application is the introduction of material into specific subcellular compartments such as the cytosol, nucleus, or even organelles of individual cells.

BRIEF DESCRIPTION OF THE DRAWINGS

Below reference is made to the accompanying drawings on which.

EXAMPLES

Materials and Methods

Chemicals

Figure 1:
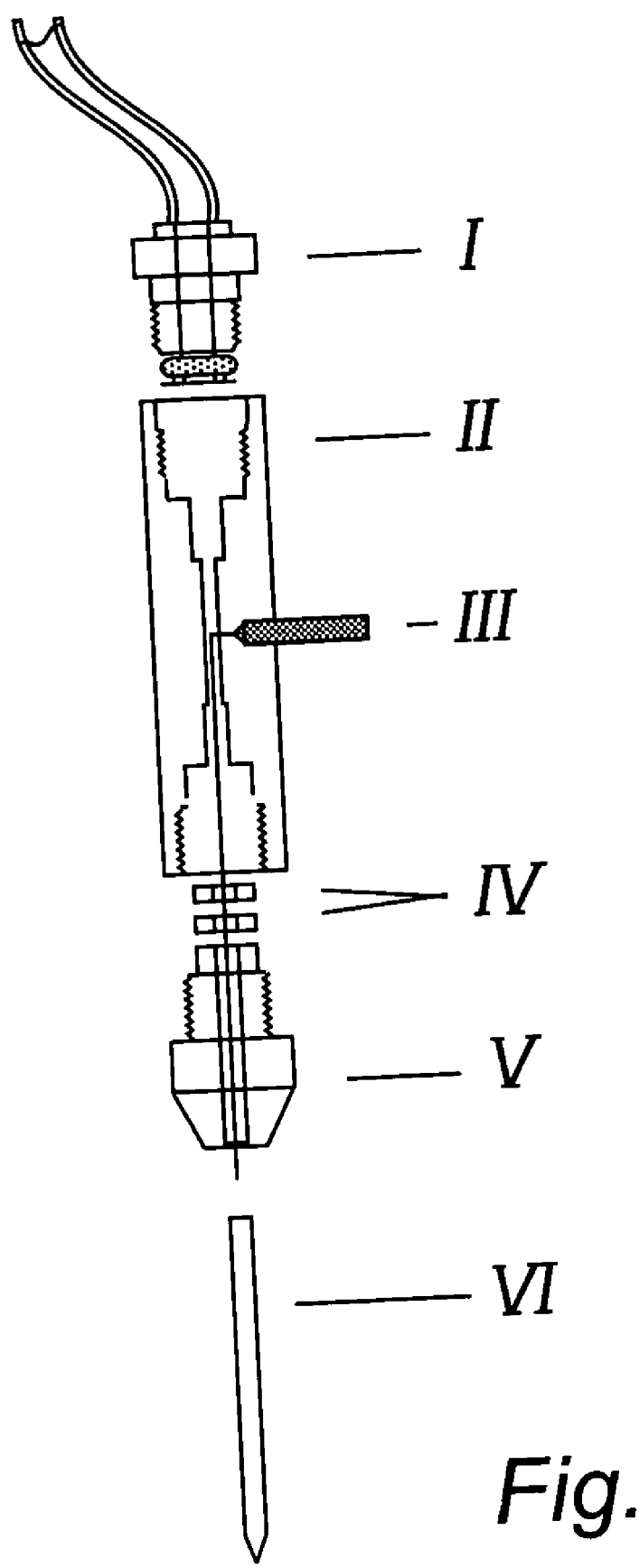
FIG. 1 is a schematic drawing of a capillary holder, consisting of a main body (II) equipped with a Pt wire electrode attached to a connector pin (III) and an entrance for the microinjector outlet (I). The injection tips (VI) are held in place by two rubber O-rings (IV) and a screwcap (V).

FM 1-43, DiO, YOYO-1 and FluoSpheres (30-nm- and 200-nm-diameter) were from Molecular probes. Fluorescein (GC-Grade), T2 DNA (168 000 bp[22]), T7 DNA (39936 bp[23]), L-α-phosphatidylcholine (type II-S), potassium phosphate (>98%) and Trizma base (>99.9%) were purchased from SIGMA. Chloroform, EDTA (titriplex III), magnesium sulfate and potassium dihydrogen phosphate (all pro analysi) were obtained from MERCK. Glycerol (>99.5%) from J. T. Baker and deionized water from a Milli-Q system (Millipore) was used.

Formation of Small Unilamellar Vesicles (SUVs)

An acetone-purified asolectin preparation dissolved in chloroform was used[24]. When preparing SUVs, the lipids were diluted with chloroform to a lipid concentration of 10 mg/ml. For a standard preparation, 300 μl of this solution was transferred to a round-bottomed flask. The solvent was removed on a rotary evaporator for about 6 h at room temperature. A thin completely dry lipid film had then formed on the walls of the flask. To this film, PBS buffer (Trizma base 5 mM, $K_3PO_4$ 30 mM, $KH_2PO_4$ 30 mM, $MgSO_4$ 1 mM, EDTA 0.5mM, pH 7.8.) containing 1% v/v glycerol, was carefully added to a lipid concentration of 1 mg/ml. The lipid film was allowed to swell overnight at 4° C.

Finally, the sample was sonicated in a bath-type sonicator filled with ice water.

A total sonication time of about 10 min was normally required before the entire lipid film dissolved and a whitish opalescent mixture was formed. The SUV-suspension was stored at 4° C. and was stable for several days.

Formation of GUVs

The formation of GUVs was performed in a two-step procedure; dehydration of the lipid dispersion followed by rehydration.

For dehydration, a small volume (5 µl) of SUV-suspension was carefully placed on a borosilicate coverslip and placed in a vacuum dessicator at 40 C. When the sample was completely dry (no sign of "fluidness" in microscope), the dehydration was terminated and the sample was allowed to reach room temperature before rehydration.

The dry sample was first rehydrated with 5 µl buffer. After 3-5 min the sample was further diluted with buffer, this was done very carefully to minimize turbulence in the sample. All rehydration liquids were at room temperature.

Micromanipulation and Electroinjection

All injection experiments were performed on an inverted microscope (Leica DM IRB, Wetzlar, Germany) equipped with a Leica PL Fluotar 40× objective and a water hydraulic micromanipulation system (high graduation manipulator: Narishige MWH-3, Tokyo, coarse manipulator: Narishige MC-35A, Tokyo).

Fluorescence imaging was achieved by sending the output of an Ar+-laser (Spectra-Physics 2025-05, 488 nm) through a 488-nm line interference filter followed by a spinning disc to break the coherence and scatter the laser light. The laser light was collected by a lens and was sent through a fluorescein filter (Leica 1-3) into the objective to excite the fluorescent dyes. The fluorescence was collected by the objective and detected by a three-chip color CCD camera (Hamamatsu, Kista, Sweden) and recorded on VHS (Panasonic S-VHS AG-5700). Digital image editing was performed using an Argus-20 system (Hamamatsu, Kista, Sweden) and Adobe Photoshop graphic software.

The electroinjections were controlled by a microinjection system (Eppendorf Transjector 5246, Hamburg, Germany) and a pulse generator (Digitimer Stimulator DS9A, Welwyn Garden City, U.K.) connected to the injection capillary.

For translation of liposomes to different locations during the experiments, carbon fiber microelectrodes (ProCFE, Axon Instruments, Foster City, Calif.) controlled by the micromanipulation system were used. By simply pushing the vesicles with the microelectrodes, they detached from the surface and adhered to the electrode tips and could be moved over long distances to a desired target. With this technique it was also possible to detach unilamellar protrusion-vesicles that adhered to multilamellar liposomes.

Preparation of Injection Tips

Injection tips were prepared from borosilicate capillaries (length: 10 cm, o.d.: 1 mm, i.d.: 0.78 mm; Clark Electromedical Instruments, Reading, UK) that were carefully flame-forged in the back ends in order to make entrance into the capillary holder easier. The capillaries were flushed with a stream of nitrogen gas before use. The tips were pulled on a $CO_2$-laser puller instrument (Model P-2000, Sutter instrument Co., Novato, Calif.). The outer diameter of the injection tips varied between 0.5-2.5 µm. To avoid contamination, tips were pulled immediately before use.

Result and Discussion

Microinjection Procedures

Figure 2:
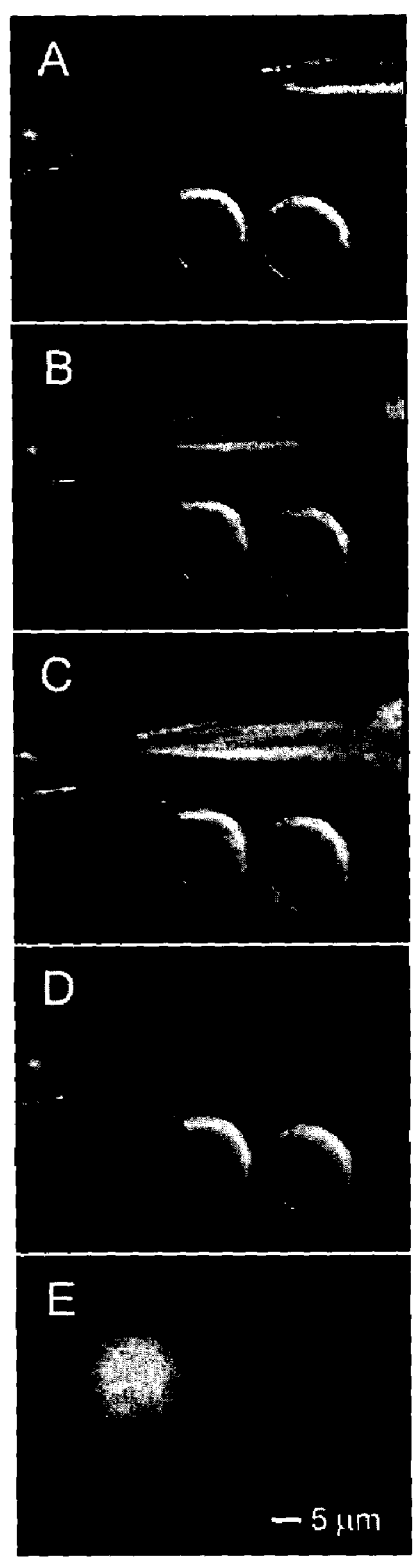
FIG. 2 illustrates electroinjection of flourescein into a giant unilamellar liposome. (A) is a Differential Interference Contrast (DIC) image showing two multilamellar liposomes with two adjacent unilamellar liposomes settled on the coverslip surface. The microelectrode and injection capillary were positioned in an opposing fashion close to the target liposome. (B) illustrates how a mechanical pressure was applied on the liposome by moving the injection tip towards the microelectrode, forcing the liposome into a kidney-like shape. (C) illustrates how the membrane was permeabilized and the liposome was slid onto the injection tip and a flourescein solution was injected into the liposome. (D) shows how the injection tip and counter electrode were removed from the liposome. (E) is a fluorescence image of the liposomes after injection. The liposome injected with flourscein is exhibiting strong fluorescence while the other liposomes were unaffected. The contour lines of the unilamellar liposomes were digitally enhanced.

The injection tips were back-filled with a medium of choice and mounted onto an in-house constructed pipet holder shown schematically in FIG. 1. The main purpose of the capillary holder is to secure the injection tip and to act as an interface between the microinjection system and the pulse generator. Basically the device is a standard patch-clamp pipet holder fitted to the outlet of a microinjection system. The main body of the pipet holder (II), in this example, was constructed from Plexiglass, and equipped with a Pt-wire electrode connected to a low-voltage pulse generator via a connector pin (III). It also comprises an entrance for the microinjector outlet (I). The injection tips (VI) are firmly held in place by two rubber O-rings (IV) secured by a Delrin screwcap (V). The pipet-holder was mounted on the micromanipulation system described above. A carbon fiber microelectrode with a tip diameter of 5 µm. After selecting an appropriate GUY or cell, the injection tip and the microelectrode were positioned in an opposing fashion, in close contact with the vesicle at an angle of 10-30° and 150-170° with respect to the object plane (see FIG. 2). By careful positioning of the electrodes it was possible to trap free-floating vesicles and subsequently perform injections. By applying a mechanical pressure in terms of moving the injection tip towards the microelectrode, forcing the vesicle into a kidney-like shape (FIG. 2B), it was possible to penetrate the membrane by applying the electric field (a rectangular dc-voltage pulse 40 V/cm, 3 ms). When permeabilized, the vesicle slid onto the injection tip and regained its spherical form (FIG. 2C). In this mode, controlled volumes of materials contained in the micropipet could be injected into the liposome. In FIG. 2C, a 25-µm solution of flourscein was injected into a single liposome. Injection volumes were controlled by the Microinjection system (injection pressure: 250-1000 hPa, time: 0.1-1.5 s). Typically, a volume of 50-to-100 fl was injected into liposomes with a diameter of 10-to-20 µm. Injection volumes for cells were kept as small as possible in order to prevent cell trauma. After completed injection, the tip was withdrawn from the interior of the vesicle without noticeable signs of vesicle damage (FIG. 2D) or leakage (FIG. 2E).

GUVs as well as cells were permeabilized in a single-pulse mode, by applying one or several transient rectangular dc-voltage pulses with pulse durations of 1-10 ms. The electric field strength was typically in the range of 10-40 V/cm. The membrane voltage $V_m$, at different loci on the membrane of a vesicle during exposure to a homogeneous electric field of duration t, can be calculated from $$V_m = 1.5\, r_s E \cos\alpha(1-\exp(-t/\tau))$$

where E is the electric field strength, $r_s$ is the radius of the sphere, $\alpha$ is the angle in relation to the direction of the electric field, and $\tau$ is the capacitive-resistive time constant. Even though this equation does not exactly match the conditions for the electroinjection technique, it can be used for roughly estimating the transmembrane potential generated. Assuming that a voltage pulse of 40 V/cm is applied at right angles over a spherical membrane container with a radius of 10 µm, a transmembrane potential of only 60 mV is generated. Clearly, such a small voltage drop across the membrane does not generate sufficient electro-compressive stress to achieve membrane permeabilization. Since the primary electrode is located inside the injection capillary, the coordinates of electric destabilization spatially coincides with the loci where maximum mechanical force is applied. This electro-mechanical permeabilization proved to be a powerful technique for penetration of lipid membranes, allowing the use of coarse micropipet tips.

Results

Figure 3:
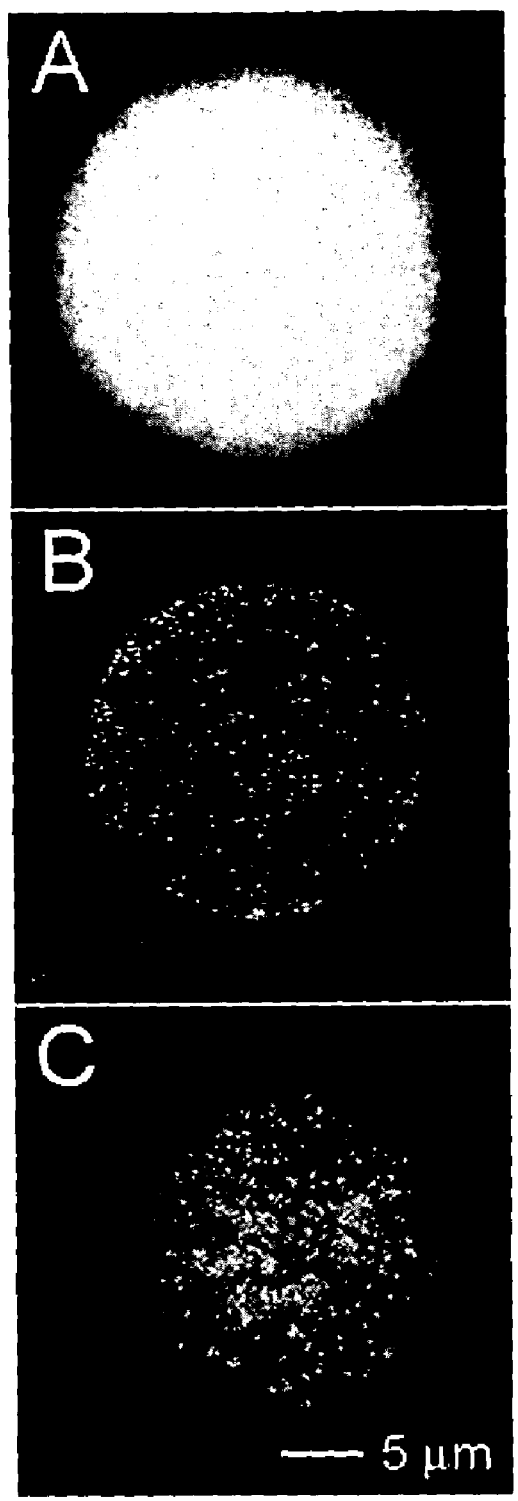
FIG. 3 illustrates injection of biopolymer and colloid particles into GUVs. The figure shows fluorescence images of unilamellar liposomes injected with highly concentrated solutions of (A) 30 nm fluorescent latex spheres, (B) small (100 nm) SBL-liposomes (50 μg/ml), stained with DiO, and (C) YOYO-1 labeled T7 DNA (5 ng/ml).

When using this procedure, we could inject reagents into single cells and GUVs with diameters of 5-to-25 μm using micropipet tips with an outer diameter of about 2 μm, or up to 3 μm. Therefore, injection into larger cells can be readily accomplished. Capillaries this coarse also have sufficiently large inner diameters for injection of larger structures and colloid particles at high concentrations into vesicles or cells. This is illustrated by the fact that YOYO-1-labeled T7 phage DNA molecules ($R_G$=0.56 μm), 30 nm latex spheres as well as 100-nm-diameter SUVs were injected into unilamellar vesicles (see FIG. 3).

Figure 4:
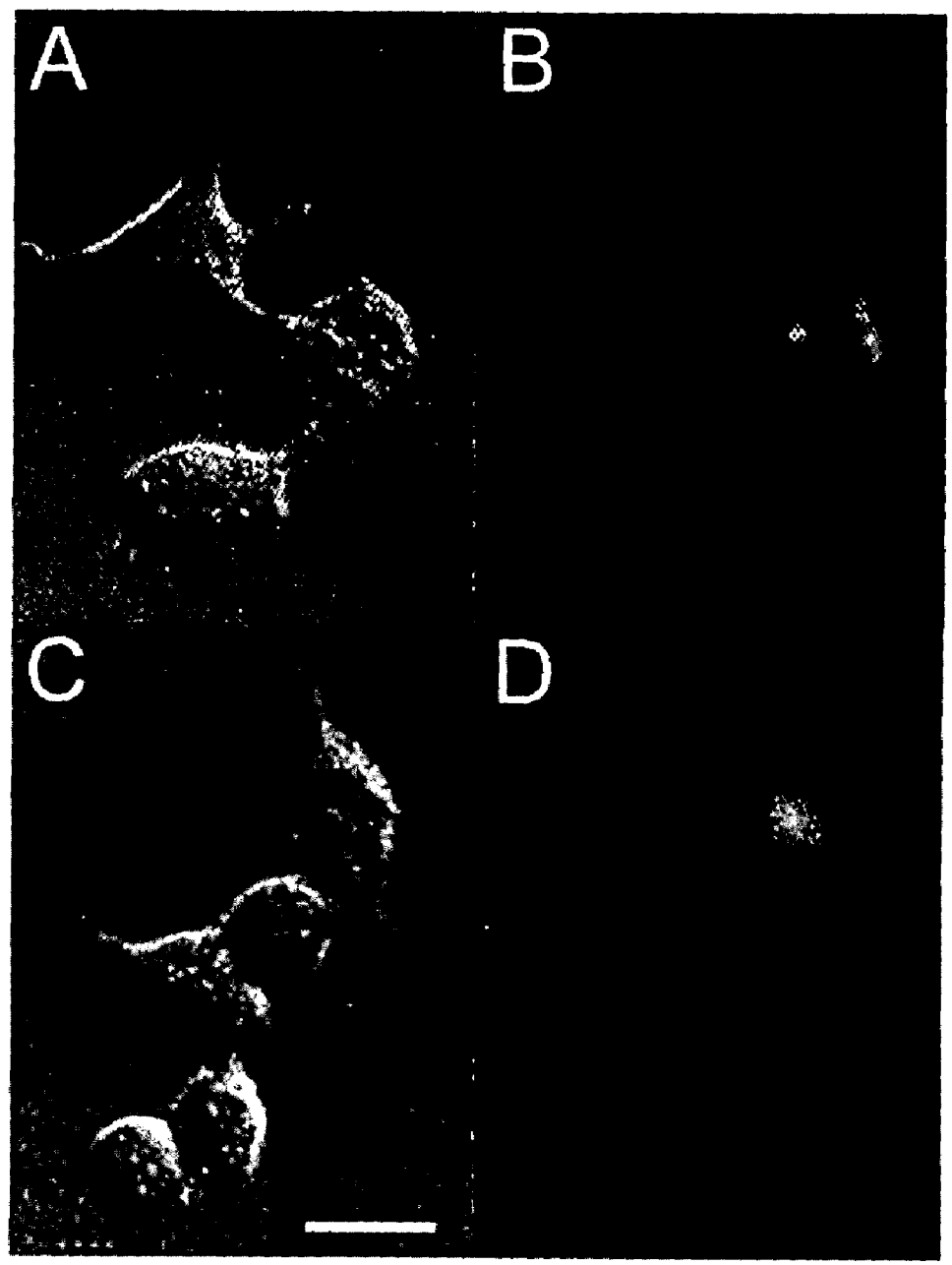
FIG. 4 illustrates electroinjection of YOYO-1-stained T7 phage DNA into PC-12 cells. (A) and (B) show brightfield and fluorescence images of cells injected with fluorescent DNA into the cytosol. In (C) and (D) DNA is injected preferentially into the nucleus of the cell and the cytosol only shows faint fluorescence.

Single PC12 cells were successfully injected with fluorescein (data not shown) as well as T7 phage DNA labeled with YOYO-1 (as shown in FIG. 4). Moreover, preferential but not exclusive injection of materials could be performed into the cytoplasm (FIG. 4B), and nucleus (FIG. 4D) of single cells. In both experiments the fluorescence is concentrated locally at the site of injection, indicating that diffusion of DNA-dye complex through the cell was restricted. This shows that the technique here presented would allow directed delivery of, for example, drugs, genetic material (such as DNA and RNA), proteins, dyes, and particles into specific compartments of a cell.

Figure 5:
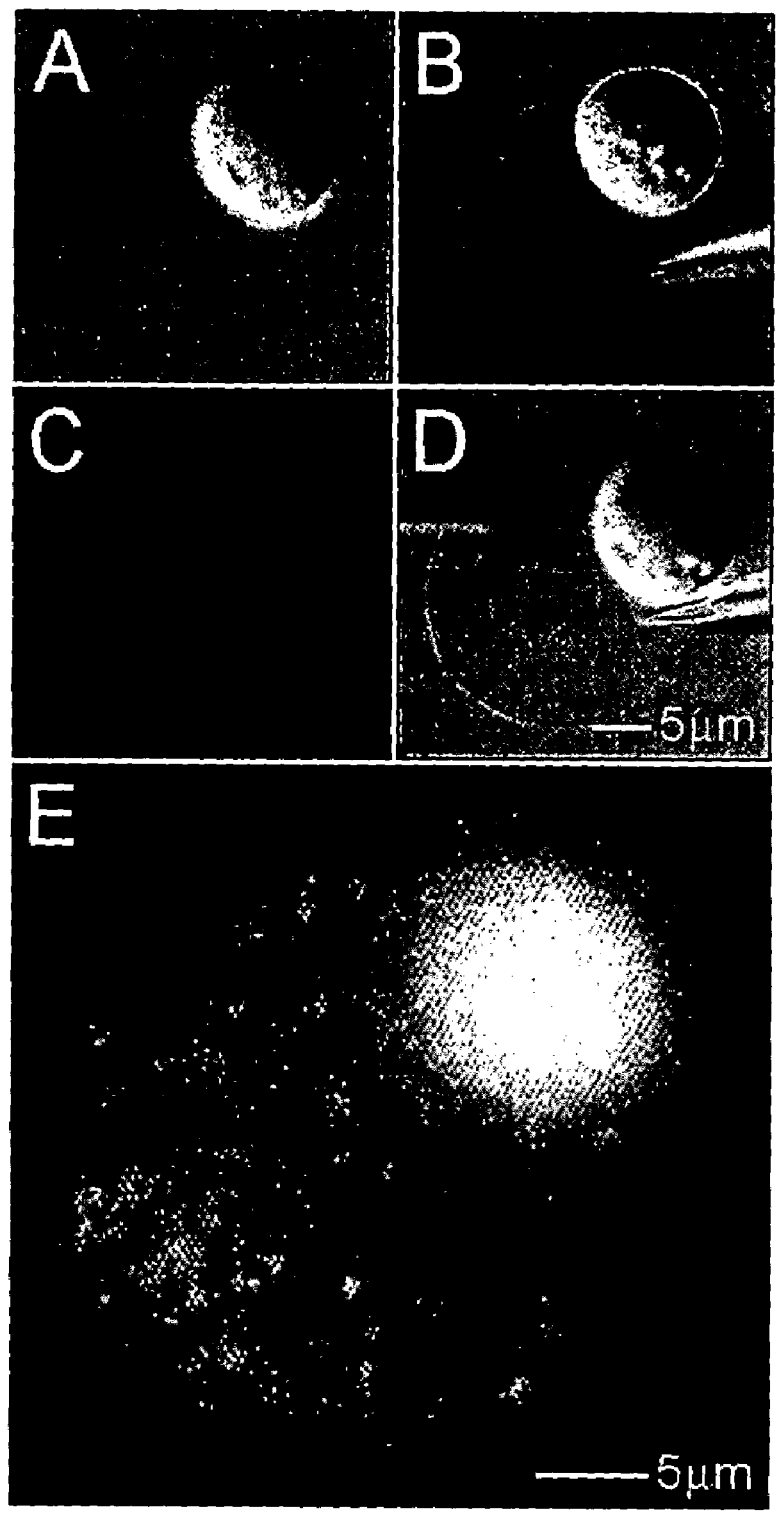
FIG. 5 shows a unilamellar liposome as a reaction container for the intercalation reaction between T2 DNA and YOYO-1. (A) shows a unilamellar protrusion from a multilamellar liposome used as target. (B) shows injection of a solution containing the T2 DNA into the liposome. (C) is a fluorescence image of the DNA-injected vesicle displaying no fluorescence. (D) shows how the injection capillary was withdrawn and replaced by a thinner capillary loaded with YOYO-1 for a second injection. (E) is a fluorescence image after incubation revealing the presence of fluorescent YOYO-1-intercalated DNA molecules inside the liposome. Brownian motion of micrometer-sized structures could be observed in the microscope, strongly suggesting that the fluorescence originated mainly from YOYO-intercalated DNA. The YOYO-1 dye, however, also had affinity for the lipid membranes as shown by the strong fluorescence originating from the multilamellar liposome.

Since the electroinjection technique described here can be performed with very high success rates, it may be a powerful tool for initiation of chemical reactions inside vesicles and cells. This is illustrated by the experiment shown in FIG. 5. By performing two consecutive injections of reagents into a single vesicle, an intercalation reaction between T2 phage DNA ($R_G$=1.1 μm) and YOYO-1 was initiated. (A) A unilamellar protrusion from a multilamellar liposome settled on the coverslip was selected as target. (B) First a solution containing the T2 DNA (1 ng/ml) was injected into the vesicle using a micropipet tip with an outer diameter of 2 μm (40 V/cm, 4 ms). (C) Fluorescence image of the DNA-injected vesicle displayed no fluorescence. (D) The injection capillary was withdrawn and replaced by a thinner capillary with an outer diameter of 1 μm loaded with YOYO-1 (50 μM), and a second injection was performed (20 V/cm, 4 ms). (E) Fluorescence imaging after 10 min incubation revealed the presence of fluorescent YOYO-1-intercalated DNA molecules inside the vesicle. Brownian motion of micrometer-sized structures could be observed in the microscope, strongly suggesting that the fluorescence originated mainly from YOYO-intercalated DNA. This experiment illustrates, except from the fact that chemical reactions can be initiated this way, also that it is possible to sequentially inject multiple reagents into a single vesicle without noticeable leakage. Initiation of complex biochemical reactions inside the confines of a liposome or cell is therefore feasible.

REFERENCES (1) Bruchez Jr, M.; Moronne, M.; Gin, P.; Weiss, S.; Alivisatos, A. P. *Scienice* 1998, 281, 2013-2016.
(2) Chan, W. C. W.; Nie, S. *Science* 1998, 281, 2016-2018.
(3) Clark, H. A.; Kopelman, R.; Tjalkens, R.; Philbert, M. A. *Anal. Chem.* 1999, 71, 4837-4843.
(4) Chourpa, I.; Morjani, H.; Riou, J.-F.; Manfait, M. *FEBS lett.* 1996, 397, 61-64.
(5) Sharonov, S.; Nabiev, I.; Chourpa, I.; Feofanov, A.; Valisa, P.; Manfait, M. J. *Raman Spectiosc.* 1994, 25, 699-707.
(6) Beljebbar, A.; Morjani, H.; Angiboust, J. F.; Sockalingum, G. D.; Polissiou, M.; Manfait, M. J. *Raman Spectrosc.* 1997, 28, 159-163.
(7) Clark, H. A.; Hoyer, M.; Philbert, M. A.; Kopelman, R. *Anal. Chem.* 1999, 71, 4831-4836.
(8) Lasic, D. D. *Liposomes: from physics to applications.* Elsevier Science B. V., Amsterdam, Nederlands, ed. 1, 1993.
(9) Bucher, P.; Fisher, A.; Luisi, P. L.; Oberholzer, T.; Walde, P. *Langmuir* 1998, 14, 2712-2721.
(10) Chiu, D. T.; Wilson, C. F.; Ryttsen, F.; Stromberg, A.; Farre, C.; Karlsson, A.; Nordbolm, S.; Gaggar, A.; Modi, B. P.; Moscho, A.; Garza-López, R. A.; Orwar, O.; Zare, R. N. *Science* 1999, 283, 1892-1895.
(11) Chiu, D. T.; Wilson, C. F.; Karlsson, A.; Danielsson, A.; Lundqvist, A.; Strömberg, A.; Ryttsén, F.; Davidson, M.; Nordholm, S., Orwar, O.; Zare, R. N. *Chem. Phys.* 1999, 247, 133-139.
(12) Oberholzer, T.; Nierbaus, K. H.; Luisi, P. L. *Biochem. Biophys. Res. Commun.* 1999, 261, 238-241.
(13) Monnard, P.-A.; Oberholzer, T.; Luisi, P. L. *Biochem. Biophys. Acta* 1997, 1329, 39-50.
(14) Shew, R. L.; Deamer, D. W. *Biochen. Biophys. Acta* 1985, 816, 1-8.
(15) Graessmann, A.; Graessmann, M.; Mueller, C. *Methods Enzymol.* 1980, 65, 816-825.
(16) Wick, R.; Angelova, M. I.; Walde, P.; Luisi, P. L. *Chem. Biol.* 1996, 3, 105-111.
(17) Davis, B. R.; Yannariello-Brown, J.; Prokopishyn, N. L.; Luo, Z.; Smith, M. R.; Wang, J.; Carsrud, N. D. V.; Brown, D. B. *Blood* 2000, 95, 437-444.
(18) Lundqvist, J. A.; Sahlin, F.; Åberg M. A. I.; Strömberg A.; Eriksson P. S.; Orwar O. *Proc. Natl. Acad. Sci. USA.* 1998, 95, 10356-10360.
(19) Weaver, J. C. *J. Cell. Biochem.* 1993, 51, 426-435.
(20) Chang, D. C.; Reese, T. S. *Biophys. J.* 1990, 58, 1-12.
(21) Kinosita, K. Jr.; Tsong, T. Y. *Nature* 1990, 268, 438-441.
(22) Harpst, J. A.; Dawson, J. R. *Biophys. J.* 1989, 55, 12371249.
(23) Oakley, J. L.; Coleman, J. E. *Proc. Nat. Acad. Sci. USA.* 1977, 74, 4266-4270.
(24) Miller, X. *J. Membr. Biol.* 1976, 26, 319-333.
(25) Needham, D.; Hochmuth, R. M. *Biophys. J.* 1989, 55, 1001-1009

The invention claimed is:

1. A method for penetration of lipid bilayer membranes comprising:
   (i) placing at least one tip of at least one hollow needle-shaped object in contact with a container comprising at least one lipid bilayer membrane, wherein the needle-shaped object comprises a first electrode, and wherein the container is between the needle-shaped object and a second electrode;
   (ii) applying mechanical pressure to the container, whereby the membrane is mechanically strained but not penetrated;
   (iii) applying a transient electric pulse of a field of strength of 1 to $10^3$ V/cm between the first electrode and the second electrode, resulting in a focused electrical field over the container resulting in a dielectric breakdown of the membrane; and
   (iv) penetrating the membrane with the at least one hollow needle-shaped object.

2. The method according to claim 1, wherein said first electrode is located inside said needle-shaped object.

3. The method according to claim 1, wherein said needle-shaped object is a micropipet.

4. The method according to claim 3, wherein said micropipet is a glass micropipet.

5. The method according to claim 3, wherein said micropipet is a quartz micropipet.

6. The method according to claim 3, wherein said micropipet is a plastic micropipet.

7. The method according to claim 1, wherein said needle-shaped object is a microelectrode.

8. The method according to claim 1, wherein said needle-shaped object is a capillary.

9. The method according to claim 1, wherein said container has a diameter of 0.1 to $10^3$ μm.

10. The method according to claim 1, wherein the tip of said needle-shaped object has an outer diameter of 1 nm to 100 μm.

11. The method according to claim 1, wherein the tip of said needle-shaped object has an inner diameter from 50 nm to up to 95 mm.

12. A microinjection method comprising performing the method for penetration of lipid bilayer membranes according to claim 1, wherein a solution or dispersion of at least one substance is delivered through said needle-shaped object and into said container once the tip of the needle-shaped object has penetrated the membrane.

13. The method according to claim 12, wherein said substance is a low or medium molecular weight substance.

14. The method according to claim 12, wherein said substance is a biopolymer.

15. The method according to claim 12, wherein said substance is a colloidal particle.

16. The method according to claim 12, wherein said substance is a nanosensor.

17. The method according to claim 12, wherein said substance is an organelle.

18. The method according to claim 12, wherein said substance is a bacterium.

19. The method according to claim 12, wherein said substance is a cell.

20. The method according to claim 1, wherein said membrane is penetrated by an array of several needle-shaped objects.

21. The method according to claim 1, wherein said first electrode is a Pt-electrode.

22. The method according to claim 1, wherein said first electrode is an Ag-electrode.

23. The method according to claim 1, wherein said first electrode is an Au-electrode.

24. The method according to claim 1, wherein said first electrode is a carbon fiber-electrode.

25. The method according to claim 1, wherein the second electrode has a diameter of approximately 1 to $10^3$ μm.

26. The method according to claim 1, wherein said second electrode is a carbon fiber-electrode.

27. The method according to claim 1, wherein said second electrode is a metal electrode.

28. The method according to claim 1, wherein said second electrode is a glass micro-electrode.

29. The method according to claim 1, wherein said container is a liposome.

30. The method according to claim 1, wherein said container is a vesicle.

31. The method according to claim 1, wherein said container is an organelle.

32. The method according to claim 1, wherein said container is a cell.

33. The method according to claim 1, wherein said container is a giant unilamellar vesicle (GUV).

34. The method according to claim 1, wherein said container is a multilamellar vesicle (MLV).

35. The method according to claim 12, which is repeated once or several times in order to insert different substances into saidcontainer.

36. The method of claim 1, further comprising delivering a substance to the container.

37. The method of claim 36, wherein the substance is delivered by microinjection.

* * * * *